United States Patent [19]
Wei et al.

[11] Patent Number: 5,891,833
[45] Date of Patent: *Apr. 6, 1999

[54] PROCESS FOR PREPARING LIQUID PERSONAL CLEANSING COMPOSITIONS WHICH PROVIDE ENHANCED PERFUME DEPOSITION

[75] Inventors: Karl Shiqing Wei; Louis Fay Wong, both of Mason; Mark Richard Sine, Morrow; Timothy Woodrow Coffindaffer, Loveland; Toan Trinh, Maineville, all of Ohio

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 667,138

[22] Filed: Jun. 20, 1996

[51] Int. Cl.$^6$ .................................. C11D 1/65; C11D 1/94
[52] U.S. Cl. ......................... 510/121; 510/473; 510/504
[58] Field of Search .................................. 510/121, 127, 510/151, 158, 403, 426, 427, 470, 473, 474, 504

[56] References Cited

U.S. PATENT DOCUMENTS

| | | | |
|---|---|---|---|
| 4,438,095 | 3/1984 | Grollier et al. | 424/70 |
| 4,673,525 | 6/1987 | Small et al. | 252/132 |
| 5,093,112 | 3/1992 | Birtwistle et al. | 424/70 |
| 5,211,883 | 5/1993 | Yamashina et al. | 252/546 |
| 5,302,322 | 4/1994 | Birtwistle et al. | 252/547 |
| 5,312,559 | 5/1994 | Kacher et al. | 252/125 |
| 5,352,386 | 10/1994 | Rahman et al. | 252/548 |
| 5,409,628 | 4/1995 | Heinz et al. | 252/174.17 |
| 5,599,483 | 2/1997 | Mizushima et al. | 510/119 |

FOREIGN PATENT DOCUMENTS

| | | | |
|---|---|---|---|
| 2712 490 | 11/1994 | France | A61K 7/075 |
| 2 177 108 | 1/1987 | United Kingdom | C11D 1/65 |
| WO 97/25975 | 7/1997 | WIPO | A61K 7/50 |

OTHER PUBLICATIONS

Document No. JP2242899AA; Date Mar. 15, 1989; Country Japan.

*Primary Examiner*—Margaret Einsmann
*Assistant Examiner*—John R. Hardee
*Attorney, Agent, or Firm*—Darryl C. Little; Tara M. Rosnell; George W. Allen

[57] ABSTRACT

A process for preparing liquid personal cleansing compositions which provides enhanced perfume deposition on the skin and which provides increased on-skin fragrance longevity. The liquid personal cleansing compositions contain from about 0.01% to about 5% of a cationic polymer; from about 1% to about 80% of an anionic surfactant; from about 0.01% to about 5% of a volatile perfume; and water. The ratio of the cationic polymer to the anionic surfactant ranges from about 1:100 to about 1:2. The process involves first forming a premix comprising the cationic polymer, the volatile perfume and water, and then adding the premix to a personal cleansing base composition which comprises anionic surfactant and water.

14 Claims, No Drawings

PROCESS FOR PREPARING LIQUID PERSONAL CLEANSING COMPOSITIONS WHICH PROVIDE ENHANCED PERFUME DEPOSITION

TECHNICAL FIELD

The present invention relates to a process for preparing liquid personal cleansing compositions which provide enhanced perfume deposition on the skin and which provide increased on-skin fragrance delivery. The process of the present invention involves forming a premix which contains a cationic material and a volatile perfume, and then adding the premix to a personal cleansing base composition which contains an anionic surfactant.

BACKGROUND OF THE INVENTION

Perfumes and fragrances are typically added to personal cleansing compositions to provide a fresh, clean impression for the compositions. Many consumers would prefer for the perfumes present in the compositions to deposit on their skin and to remain there for an extended period of time to convey a lasting impression of freshness. However, due to the volatility of many perfumes, it can be difficult to deliver this benefit to consumers.

Cationic deposition polymers have been used in the past to enhance deposition of certain nonvolatile components from shampoos and other personal cleansing compositions. For example, U.S. Pat. Nos. 5,037,818 and 5,085,857 describe the use of cationic guar gum to enhance the deposition of antidandruff particles and insoluble nonvolatile silicone respectively. Deposition polymers have also been proposed to enhance the deposition of sunscreen materials from a shampoo composition. In EP 386 898 a cationic polygalactomannan gum derivative is used. WO 95/22311 describes the use of certain cationic polymers to increase the deposition of nonvolatile benefit agents which include silicones, fats and oils, waxes, hydrocarbons, fatty acids and fatty alcohols, lipids, vitamins and sunscreens.

It would be desirable, however, to increase the deposition of volatile ingredients, such as perfumes, and to provide increased on-skin longevity with respect to these ingredients. This benefit is provided by the present invention.

SUMMARY OF THE INVENTION

The present invention relates to a process for preparing liquid personal cleansing compositions which provides enhanced perfume deposition on the skin and which provides increased on-skin fragrance longevity. The liquid personal cleansing compositions prepared according to the process of the present invention comprise: a) from about 0.01% to about 5% of a cationic material; b) from about 1% to about 80% of a surfactant selected from the group consisting of anionic surfactants, amphoteric surfactants which have been altered to have a negative charge, and mixtures thereof; c) from about 0.01% to about 5% of a volatile perfume; and d) water. The ratio of the cationic material to the group (b) surfactant present in the liquid personal cleansing compositions of the present invention ranges from about 1:100 to about 1:2. The process for preparing the liquid personal cleansing compositions involves first forming a premix comprising the cationic material, the volatile perfume and water, and then adding the premix to a personal cleansing base composition which comprises the group (b) surfactant and water.

DETAILED DESCRIPTION OF THE INVENTION

The present invention is directed to a process for preparing liquid personal cleansing compositions which provide enhanced perfume deposition on the skin and which provide increased on-skin fragrance longevity. The liquid personal cleansing compositions of the present invention comprise a cationic material, a volatile perfume, a surfactant selected from the group consisting of anionic surfactant, negatively charged amphoteric surfactants, and mixtures thereof, and water. As used herein, "personal cleansing compositions" refers to any cleansing composition which can be used on the human body. Such compositions would include, for example, shower gel compositions, hand soaps and shampoos.

The process of the present invention involves first forming a premix comprising the cationic material, the volatile perfume and water, and then adding the premix to a personal cleansing base composition which comprises the group (b) surfactant and water to form liquid personal cleansing compositions. The liquid personal cleansing compositions comprise from about 1% to about 50%, preferably from about 5% to about 50% more preferably from about 10% to about 50% of the premix and from about 50% to about 99%, preferably from about 50% to about 95%, more preferably from about 50% to about 90% of the base personal cleansing composition. The process of the present invention and the liquid personal cleansing shower gel compositions prepared according to the process are described in detail as follows:

I. The Process Steps

A. Forming a Premix

The process of the present invention involves as a first step, preparing a premix comprised of a cationic material, a volatile perfume and water. Each of the ingredients comprising the premix is described in detail as follows:

1. The Cationic Material

The premix formed in the first step of the process of the present invention comprises from about 0.1% to about 10%, preferably from about 1% to about 10%, more preferably from about 1% to about 5% of a cationic material. The level of cationic material present in the premix is selected so that the level of cationic material in the final liquid personal cleansing composition ranges from about 0.01% to about 5%, preferably from about 0.1% to about 2%, more preferably from about 0.2% to about 1%, even more preferably from about 0.5% to about 1%, and most preferably from about 0.67% to about 1%. The cationic materials useful in the premix herein include, for example, cationic polymers, quaternary fabric softeners, and cationic surfactants. Cationic polymers are preferred for use as the cationic material herein.

Suitable cationic polymers for use in the present invention include cationic polysaccharides, cationic copolymers of saccharides and cationic monomers, cationic copolymers of acrylamide and cationic monomers, and synthetic cationic polymers.

The cationic polysaccharide class encompasses those polymers based on 5 or 6 carbon sugars and derivatives which have been made cationic by engrafting of cationic moieties on the polysaccharide backbone. They may be composed of one type of sugar or of more than one type, i.e. copolymers of the above derivatives and cationic materials. The monomers may be in straight chain or branched chain geometric arrangements. Cationic polysaccharide polymer include the following: cationic celluloses and hydroxyethylcelluloses; cationic starches and hydroxyalkyl starches; cationic polymers based on arabinose monomers such as those which could be derived from arabinose vegetable gums; cationic polymers derived from xylose polymers found in materials such as wood, straw, cottonseed hulls, and corn cobs; cationic polymers derived from fucose polymers found as a component of cell walls in seaweed; cationic polymers derived from fructose polymers such as Inulin found in certain plants; cationic polymers based on acid-containing sugars such as galacturonic acid and glucuronic acid; cationic polymers based on amine sugars such as galactosamine and glucosamine; cationic polymers based on 5 and 6 membered ring polyalcohols; cationic polymers based on galactose monomers which occur in plant gums and mucilages; cationic polymers based on mannose monomers such as those found in plants, yeasts, and red algae; cationic polymers based on the galactomannan copolymer known as guar gum obtained from the endosperm of the guar bean.

Specific examples of members of the cationic polysaccharide class include the cationic hydroxyethyl cellulose JR 400 made by Union Carbide Corporation; the cationic starches Stalok® 100, 200, 300 and 400 made by Staley, Inc.; the cationic galactomannans based on guar gum of the Galactasol 800 series by Henkel, Inc. and the Jaguar Series by Celanese Corporation.

Preferred cationic polysaccharides include those of the cationic guar gum class with molecular weights of about 1,000 to about 3,000,000. More preferred molecular weights are from about 2,500 to about 2,000,000. These polymers have a polysaccharide backbone comprised of galactomannan units and a degree of cationic substitution ranging from about 0.04 per anhydroglucose unit to about 0.80 per anhydroglucose unit with the substituent cationic group being the adduct of 2,3-epoxypropyltrimethyl ammonium chloride to the natural polysaccharide backbone. Examples are Jaguar C-14-S, C-15 and C-17 sold by Celanese Corporation. In order to achieve the benefits described in this invention, the polymer must have characteristics, either structural or physical which allow it to be suitably and fully hydrated and subsequently well incorporated into the liquid personal cleansing compositions.

The cationic copolymers of saccharides and synthetic cationic monomers useful in the present invention encompass those containing the following saccharides: glucose, galactose, mannose, arabinose, xylose, fucose, fructose, glucosamine, galactosamine, glucuronic acid, galacturonic acid, and 5 or 6 membered ring polyalcohols. Also included are hydroxymethyl, hydroxyethyl and hydroxypropyl derivatives of the above sugars. When saccharides are bonded to each other in the copolymers, they may be bonded via any of several arrangements, such as 1,4-α; 1,4-β; 1,3-α; 1,3-β and 1,6 linkages. The synthetic cationic monomers for use in these copolymers can include dimethyldiallylammonium chloride, dimethylaminoethylmethylacrylate, diethyldiallylammonium chloride, N,N-diallyl,N-N-dialkyl ammonium halides, and the like.

Examples of members of the class of copolymers of saccharides and synthetic cationic monomers include those composed of cellulose derivatives (e.g., hydroxyethyl cellulose) and N,N-diallyl,N-N-dialkyl ammonium chloride available from National Starch Corporation under the tradename Celquat.

The cationic copolymers of acrylamide and synthetic cationic monomers useful in the present invention are those having the formula

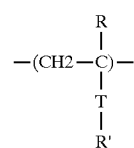

where:
T is —O— or —C(=O)—
R is H or CH3
and R' is —NH—(CH$_2$)$_n$—N$^+$(CH$_3$)$_3$X$^-$ or —O—(CH$_2$)$_n$—N$^+$(CH$_3$)$_3$X$^-$
in which n is an integer from 1 to 4 and X is selected from Cl, Br, I, and CH$_3$SO$_3$. In particular, the copolymer of acrylamide and acrylamido propyl trimethyl ammonium chloride is preferred. This polymer is made by Allied Colloids under the trade name of SALCARE SC60.

The cationic synthetic polymers useful in the present invention are cationic polyalkylene imines, ethoxypolyalkylene imines, and poly[N-[-3-(dimethylamrnmonio)propyl]-N'-[3-(ethyleneoxyethylene dimethylammonio)propyl]urea dichloride ] the latter of which is available from Miranol Chemical Company, Inc. under the trademark of Miranol A-15, CAS Reg. No. 68555-36-2.

It is preferred that the cationic polymers used herein be fully hydrated.

2. The Volatile Perfume

The premix formed in the first step of the process of the present invention also contains from about 0.1% to about 10%, preferably from about 1% to about 10%, more preferably from about % to about 5%, and most preferably from about 2% to about 5% of a volatile perfume. The level of volatile perfume present in the premix is selected so that the level of volatile perfume present in the final liquid personal cleansing composition ranges from about 0.01% to about 5%, preferably from about 0.1% to about 4%, more preferably from about 0.2% to about 2%, and most preferably from about 0.4% to about 2%.

The volatile perfume ingredients employed in the personal cleansing compositions of the present invention are the conventional ones known in the art. Selection of the perfume ingredients used in the liquid personal cleansing shower gel compositions of the present invention is based solely on the desired fragrance characteristics for the composition.

Suitable perfume compounds and compositions can be found in the art including U.S. Pat. Nos.: 4,145,184, Brain and Cummins, issued Mar. 20, 1979; 4,209,417, Whyte, issued Jun. 24, 1980; 4,515,705, Moeddel, issued May 7, 1985; and 4,152,272, Young, issued May 1, 1979, all of said patents being incorporated herein by reference.

Perfumes can be classified according to their volatility. For purposes of the present invention, "volatile" perfumes are those having a boiling point of less than about 500° C. The highly volatile, low boiling, perfume ingredients typically have boiling points of about 250° C. or lower. The moderately volatile perfume ingredients are those having boiling points of from about 250° C. to about 300° C. The less volatile, high boiling, perfume ingredients are those having boiling points of about from about 300° C. to about 500° C. Many of the perfume ingredients as discussed hereinafter, along with their odor and/or flavor characters, and their physical and chemical properties, such as boiling point and molecular weight, are given in "Perfume and Flavor Chemicals (Aroma Chemicals)," Steffen Arctander, published by the author, 1969, incorporated herein by reference. It is preferred that the liquid personal cleansing products herein contain at least about 5%, more preferably about 25%, and most preferably at least about 50% of highly volatile perfume ingredients having a boiling point of 250° C. or lower.

Examples of the highly volatile, low boiling, perfume ingredients are: anethole, benzaldehyde, benzyl acetate, benzyl alcohol, benzyl formate, iso-bornyl acetate, camphene, cis-citral (neral), citronellal, citronellol, citronellyl acetate, para-cymene, decanal, dihydrolinalool, dihydromyrcenol, dimethyl phenyl carbinol, eucalyptol, geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, alpha-pinene, beta-pinene, gamma-terpinene, alpha-terpineol, beta-terpineol, terpinyl acetate, and vertenex (para-tertiary-butyl cyclohexyl acetate). Some natural oils also contain large percentages of highly volatile perfume ingredients. For example, lavandin contains as major components: linalool; linalyl acetate; geraniol; and citronellol. Lemon oil and orange terpenes both contain about 95% of d-limonene.

Examples of moderately volatile perfume ingredients are: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, flor acetate, heliotropine, 3-cis-hexenyl salicylate, hexyl salicylate, lilial (para-tertiarybutyl-alpha-methyl hydrocinnamic aldehyde), gamma-methyl ionone, nerolidol, patchouli alcohol, phenyl hexanol, beta-selicarb, trichloromethyl phenyl carbinyl acetate, triethyl citrate, vanillin, and veratraldehyde. Cedarwood terpenes are composed mainly of alpha-cedrene, beta-cedrene, and other $C_{15}H_{24}$ sesquiterpenes.

Examples of the less volatile, high boiling, perfume ingredients are: benzophenone, benzyl salicylate, ethylene brassylate, galaxolide (1,3,4,6,7,8-hexahydro-4, 6,6,7,8,8-hexamethyl-cyclopenta-gama-2-benzopyran) hexyl cinnamic aldehyde, lyral (4-(4-hydroxy-4-methyl pentyl)-3-cyclohexene-10-carboxaldehyde), methyl cedrylone, methyl dihydro jasmonate, methyl-beta-naphthyl ketone, musk indanone, musk ketone, musk tibetene, and phenylethyl phenyl acetate.

3. Water

The premix formed in the first step of the process of the present invention also typically contains from about 80% to about 99%, preferably from about 90% to about 99%, more preferably from about 95% to about 99% of water. The level of water present in the premix is selected so that the total water level present in the final liquid personal cleansing composition (from premix and base) ranges from about 20% to about 95%, preferably from about 40% to about 90%, more preferably from about 60% to about 90%, and most preferably from about 70% to about 90%.

B. Adding the Premix to a Personal Cleansing Base Composition

Next, the process of the present invention involves adding the premix to a base personal cleansing composition. The ingredients comprising the base personal cleansing composition are described in detail as follows:

C. The Surfactants

The liquid personal cleansing compositions of the present invention also contain from about 1% to about 80%, preferably from about 2% to about 50%, more preferably from about 3% to about 30% and most preferably from about 3% to about 10% of an anionic surfactant.

1. The Anionic Surfactant

A highly preferred anionic surfactant for use in the compositions herein is alkyl ether sulphate of formula:

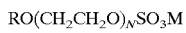

$$RO(CH_2CH_2O)_N SO_3 M$$

where R is an alkyl or alkenyl group of 8 to 24 carbon atoms, n ranges from about 0.5 to about 10 especially about 1.5 to about 8, and M is a cation such as ammonium, alkanolamines, such as triethanolamine, monovalent metals, such as sodium and potassium, and polyvalent metal cations, such as magnesium, and calcium. The cation M, of the anionic detersive surfactant should be chosen such that the detersive surfactant component is water soluble. Solubility will depend upon the particular anionic detersive surfactants and cations chosen.

Preferably, R has from about 8 to about 18 carbon atoms, more preferably from about 10 to about 16 carbon atoms, most preferably from about 12 to about 14 carbon atoms in both the alkyl and alkyl ether sulfates. The alkyl ether sulfates are typically made as condensation products of ethylene oxide and monohydric alcohols having from about 8 to about 24 carbon atoms. The alcohols can be derived from fats, e.g., coconut oil, palm kernal or tallow, or can be synthetic. Lauryl alcohol and straight chain alcohols derived from coconut oil or palm kernel are preferred herein. Such alcohols are reacted with between about 1 and about 10, and especially about 3, molar proportions of ethylene oxide and the resulting mixture of molecular species having, for example, an average of 3 moles of ethylene oxide per mole of alcohol, is sulfated and neutralized.

Highly preferred alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide.

Other anionic detersive surfactants which can be used in the compositions herein are the water-soluble salts of organic, sulfuric acid reaction products of the general formula $[R_1—SO_3—M]$ where $R_1$ is selected from the group consisting of a straight or branched chain, saturated aliphatic hydrocarbon radical having from about 8 to about 24, preferably about 10 to about 18, carbon atoms; and M is a cation, as previously described, subject to the same limitations regarding polyvalent metal cations as previously discussed. Examples of such detersive surfactants are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10-18}$ n-paraffins.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. No. 2,486,921; U.S. Pat. No. 2,486,922; and U.S. Pat. No. 2,396,278, which descriptions are incorporated herein by reference.

Other anionic detersive surfactants suitable for use in the personal cleansing compositions are the succinnates, examples of which include disodium N-octadecylsulfosuccinnate; disodium lauryl sulfosuccinate; diammonium lauryl sulfosuccinate; tetrasodium N-(1, 2-dicarboxyethyl)-N-octadecylsulfosuccinnate; diamyl ester of sodium sulfosuccinic acid; dihexyl ester of sodium sulfosuccinic acid; dioctyl esters of sodium sulfosuccinic acid.

Other suitable anionic detersive surfactants include olefin sulfonates having about 10 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The alpha-olefins from which the olefin sulfonates are derived are mono-olefins having about 10 to about 24 carbon atoms, preferably about 12 to about 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific alpha-olefin sulfonate mixture of the above type is described more fully in the U.S. Pat. No. 3,332,880, which description is incorporated herein by reference.

Another class of anionic detersive surfactants suitable for use in the personal cleansing compositions are the beta-alkyloxy alkane sulfonates. These compounds have the following formula:

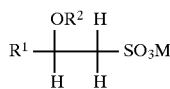

where $R^1$ is a straight chain alkyl group having from about 6 to about 20 carbon atoms, $R^2$ is a lower alkyl group having from about 1 (preferred) to about 3 carbon atoms, and M is a water-soluble cation as hereinbefore described.

Preferred additional anionic detersive surfactants for use in the personal cleansing compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium potassium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

It is noted that an amphoteric surfactant which has been altered to have a negative charge can be used in the liquid personal cleansing compositions herein instead of the anionic surfactant or in combination with the anionic surfactant. The charge of the amphoteric surfactant can be altered by conventional means, for example, by adjusting the pH of a surfactant solution containing the amphoteric surfactant.

The anionic or negatively charged amphoteric surfactant may be used in combination with soaps and/or other synthetic detergent surfactants. While the synthetic detergent surfactant can be selected from any known surfactant suitable for topical application to the human body, the synthetic detergent surfactant is preferably a mild lathering synthetic detergent surfactant. The optional synthetic detergent surfactant is typically selected from the group consisting of: nonionic surfactants, amphoteric and zwitterionic surfactants, cationic surfactants and mixtures thereof. Both low and high lathering and high and low water-soluble surfactants can be used in the liquid personal cleansing compositions of the present invention. Suds boosting synthetic detergent surfactants and/or synthetic detergent surfactants that are known as good dispersants for soap curds that are formed in hard water, are particularly desirable.

2. Amphoteric Surfactant

In a preferred embodiment of the present invention, the liquid personal cleansing compositions contain from about 1% to about 20%, preferably from about 1.5% to about 10%, more preferably from about 2% to about 8% of an amphoteric surfactant. When an amphoteric surfactant is employed in the compositions herein, the ratio of the anionic:amphoteric surfactant is preferably less than about 2:1, preferably less than about 3:2.

Suitable amphoteric surfactant components for use in the liquid personal cleansing compositions herein include those which are known for use in personal cleansing compositions or other personal care cleansing composition, and which contain a group that is anionic at the pH of the personal cleansing composition. Concentration of such surfactant components in the personal cleansing composition preferably ranges from about 0.5% to about 20%, preferably from about 1% to about 10%, more preferably from about 2% to about 5% by weight of the composition. Examples of amphoteric surfactants suitable for use in the personal cleansing composition herein are described in U.S. Pat. No. 5,104,646 (Bolich Jr. et al.), U.S. Pat. No. 5,106,609 (Bolich Jr. et al.), which descriptions are incorporated herein by reference. Examples of amphoteric detersive surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "MIRANOL"™ and described in U.S. Pat. No. 2,528,378.

Other amphoterics, sometimes classified as zwitterionics, such as betaines can also useful in the present invention. Such zwitterionics are considered as amphoterics in the present invention where the zwitterionic has an attached group that is anionic at the pH of the composition. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention. Most preferred for use herein is cocoamidopropyl betaine.

Other surfactants which can optionally be employed in the compositions herein are disclosed in the following U.S. Patents, all of which are herein incorporated by reference:

| U.S. Pat. No. | Issue Date | Inventor(s) |
|---|---|---|
| 4,061,602 | 12/1977 | Oberstar et al. |
| 4,234,464 | 11/1980 | Morshauser |
| 4,472,297 | 9/1984 | Bolich et al. |
| 4,491,539 | 1/1985 | Hoskins et al. |
| 4,540,507 | 9/1985 | Grollier |
| 4,565,647 | 1/1986 | Llenado |
| 4,673,525 | 6/1987 | Small et al. |
| 4,704,224 | 11/1987 | Saud |
| 4,788,006 | 11/1988 | Bolich, Jr., et al. |
| 4,812,253 | 3/1989 | Small et al. |
| 4,820,447 | 4/1989 | Medcalf et al. |
| 4,906,459 | 3/1990 | Cobb et al. |
| 4,923,635 | 5/1990 | Simion et al. |
| 4,954,282 | 9/1990 | Rys et al. |

The total level of surfactant present in the liquid personal cleansing compositions of the present invention typically ranges from about 1% to about 80%, preferably from about 2% to about 50%, more preferably from about 5% to about 30% and most preferably from about 5% to about 20% by weight of the compositions.

2. Water

The base personal cleansing compositions used in the process of the present invention also contain water. The level of water in the base personal cleansing composition is selected so that the total level of water in the final liquid personal cleansing composition (including premix and base) ranges from about 20% to about 95%, preferably from about 40% to about 90%, more preferably from about 60% to about 90% and most preferably from about 70% to about 90%.

3. Other Optional Ingredients

The base personal cleansing composition used in the process of this invention can also include other optional ingredients. The levels of these ingredients, when used, is selected so that they are present in the final personal cleansing composition at from about 1% to about 65%, preferably from about 5% to about 50%, more preferably from about 5% to about 20%. All levels described herein for the optional ingredients are for the final liquid personal cleansing composition. The levels of the optional ingredients present in the base shower gel compositions are selected so that the level of that ingredient in the final composition is within the target range for the final composition.

Examples of optional ingredients which can desirably be employed in the base liquid personal cleansing compositions of the present invention include, for example, compatible salt and salt hydrates as fillers. Some preferred salts are sodium chloride, sodium sulfate, disodium hydrogen phosphate, sodium pyrophosphate, sodium tetraborate.

Generally, compatible salts and salt hydrates include the sodium, potassium, magnesium, calcium, aluminum, lithium, and ammonium salts of inorganic acids and small (6 carbons or less) carboxylic or other organic acids, corresponding hydrates, and mixtures thereof, are applicable. The inorganic salts include chloride, bromide, sulfate, metasilicate, orthophosphate, pyrophosphate, polyphosphate, metaborate, tetraborate, and carbonate. The organic salts include acetate, formate, methyl sulfate, and citrate.

Water-soluble amine salts can also be used. Monoethanolamine, diethanolamine, and triethanolamine (TEA) chloride salts are preferred.

Aluminosilicates and other clays are also useful in the present invention. Some preferred clays are disclosed in U.S. Pat. Nos. 4,605,509 and 4,274,975, incorporated herein by reference.

Other types of clays include zeolite, kaolinite, montmorillonite, attapulgite, illite, bentonite, and halloysite. Another preferred clay is kaolin.

The liquid personal cleansing compositions of the present invention can contain also other additives commonly included in personal cleansing compositions such as sanitizing or antimicrobial agents, dyes, conditioning/moisturizing agents, preservatives and the like.

Liquid personal cleansing of the present invention can contain silicone gum or fluid, as described in U.S. Pat. Nos.: 4,906,459, Cobb et al., issued Mar. 6, 1990; 4,788,006, Bolich, Jr. et al., issued Nov. 29, 1988; 4,741,855, Grote et al., issued May 3, 1988; 4,728,457, Fieler et al., issued Mar. 1, 1988; 4,704,272, Oh et al., issued Nov. 3, 1987; and 2,826,551, Geen, issued Mar. 11, 1958, all of said patents being incorporated herein by reference.

The silicone component can be present in the liquid personal cleansing compositions of the present invention at a level which is effective to deliver a skin mildness benefit, for example, from about 0.5% to about 20%, preferably from about 1.5% to about 16%, and most preferably from about 3% to about 12% of the composition. Silicone fluid, as used herein, denotes a silicone with viscosities ranging from about 5 to about 600,000 centistokes, most preferably from about 350 to about 100,000 centistokes, at 25° C. Silicone gum, as used herein, denotes a silicone with a mass molecular weight of from about 200,000 to about 1,000,000 and with a viscosity of greater than about 600,000 centistokes. The molecular weight and viscosity of the particular selected siloxanes will determine whether it is a gum or a fluid. The silicone gum and fluid can also be mixed together and incorporated into the compositions of the present invention.

The base personal cleansing compositions herein can also optionally contain a neat fragrance.

The levels set out in Other Ingredients Table below are particularly illustrative for liquid personal cleansing compositions containing other optional ingredients.

OTHER INGREDIENTS TABLE
Practical Wt. % of Other Ingredients

| Preferred | More Preferred | Most Preferred | |
|---|---|---|---|
| Filler Salts and Salt Hydrates | 0.5–50% | 0.75–25% | 1–15% |
| Water-Soluble Organics | 1.0–50% | 2–40% | 5–20% |
| Polymeric Mildness Enhancers | 0.25%–20% | 0.5%–10% | 1–5% |
| Other Impalpable Water-insolubles | 1–60% | 2–30% | 4–25% |
| Aluminosilicates/Clay | 0.5–25% | 1–10% | 3–8% |

II. The Liquid Personal Cleansing Compositions

The liquid personal cleansing compositions of the present invention have a viscosity ranging from about 100 to about 100,000 centipoise, preferably from about 1,000 to about 50,000 centipoise, most preferably from about 5,000 to about 10,000 centipoise.

The ratio of the cationic material to anionic surfactant in the liquid personal cleansing compositions of the present invention ranges from about 1:100 to about 1:2, preferably from about 1:50 to about 1:5, more preferably from about 1:30 to about 1:5, even more preferably from about 1:20 to about 1:5, and most preferably from about 1:15 to about 1:5.

Without being bound by theory, it is believed that the cationic material and the anionic surfactant present in the personal cleansing compositions herein form coacervates or ion-pairs and that the perfume becomes physically entrapped within the coacervate or ion-pair. The coacervate is believed to deposit onto the skin during the wash/rinse process, thus significantly enhancing deposition of the perfume entrapped therein. It is further believed that the slow release of perfume from the coacervate provides a fragrance longevity benefit.

If the ratio of cationic material:anionic surfactant is less than about 1:100 or greater than about 1:2, the formation of the coacervate is believed to be impeded and the benefit of the invention (e.g., enhanced deposition of perfume and increased longevity of fragrance) is reduced or eliminated and/or the product is rendered physically unstable.

In addition to the ratio of the cationic material to the anionic surfactant, coacervate formation is also dependent upon a variety of other criteria such as molecular weight, component concentration, ionic strength (including modification of ionic strength, for example, by addition of salts), charge density of the cationic and anionic components, pH, and temperature. Coacervate systems and the effect of these parameters have been described, for example, by J. Caelles, et al., "Anionic and Cationic Compounds in Mixed Systems", *Cosmetics & Toiletries*, Vol. 106, April 1991, pp 49–54, C. J. van Oss, "Coacervation, Complex-Coacervation and Flocculation", *J. Dispersion Science and Technology*, Vol. 9 (5,6), 1988–89, pp 561–573, and D. J. Burgess, "Practical Analysis of Complex Coacervate Systems", *J. of Colloid and Interface Science*, Vol. 140, No. 1, November 1990, pp 227–238, which descriptions are incorporated herein by reference.

Techniques for analysis of formation of complex coacervates are known in the art. For example, microscopic analyses of the personal cleansing compositions, can be utilized to identify whether a coacervate phase has formed. Such coacervate phase will be identifiable as an additional emulsified phase in the composition. The use of dyes can aid in distinguishing the coacervate phase from other insoluble phases dispersed in the personal cleansing composition.

The liquid personal cleansing compositions of the present invention provide enhanced deposition of the fragrance on the skin and provide increased on-skin fragrance longevity.

ANALYTICAL METHODS

1. GC/MS Method for Measuring Perfume Deposition

1. The skin background is extracted using 5×5 cc acetone for about 30 seconds on the forearm (area about 20 $cm^2$).

2. One forearm is washed with test product and the other forearm is washed with a control product using a standard arm washing protocol (below).

3. The total perfume deposited on each arm is extracted using 5×5 cc acetone for about 30 seconds (area of about 20 $cc^2$).

4. The extracted acetone solution from step 3 is preconcentrated to about 0.5 ml by turbovap.

5. The perfume components are analyzed and quantitated by GC/MS.

Standard Arm Washing Protocol

1. Run laboratory tap water at low/moderate flow at about 90°–100° F. Leave water running throughout the entire washing procedure.

2. Wet the volar portion on the forearm for about 10 seconds.

3. Apply about 1 cc product to the forearm.

4. Rub the product from the wrist to the elbow for about 10 seconds to create a lather.

5. Allow the lather to remain on the skin for about 90 seconds.

6. Rinse forearm for about 15 seconds with running water, allowing the water stream to hit the lather line on the skin and run down the forearm.

7. Pat the forearm dry with paper towels.

2. Wash Cloth Method for Measuring Perfume Intensity

1. Standard white washcloths are cut into approximately 3"×3" swatches.

2. The swatch is placed under running tap water (about 95°–100 ° F.) for 5 seconds.

3. About one (1) cc of test product is placed onto wash cloth.

4. The cloth is rubbed in between hands for about 15 seconds to generate lather.

5. The lather is allowed to remain on the cloth for about 30 seconds.

6. The cloth is rinsed by holding the cloth in the corner and placing it under running tap water (about 95°–100° F.) for about 15 seconds.

7. The cloth is held in the comer and allowed to drip dry for about 5 seconds.

8. The cloth is placed between 2 Bounty paper towels folded in half and patted for about 5 seconds.

9. The dry portion of each Bounty towel is then folded over again and patted for about another 5 seconds.

10. Steps 1–9 are repeated for control product.

11. Each cloth (the one with the test product and the one with the control product) is placed on top of a 4 oz. glass jar and allowed to dry overnight. (Do not place lid on jar.)

11. Each dried cloth is placed inside a glass jar. (Do not put lid on jar).

12. Ten panelists evaluate the odor intensity of the cloth inside each jar according to the following scale:

Scale is from 0 to 100:

0=no perfume odor

25=slight perfume odor

50=moderate perfume odor

100=strong perfume odor

The panelists can assign any number between 0 and 100. The numbers 0, 25, 50 and 100 are only intended as guidelines and are not to be viewed as the only numbers that can be assigned.

13. The panelists also indicate any perceived difference in the intensity of the two wash clothes by using a 0 to 4 difference scale:

0=equal/no difference

1=I think they are different

2=I know they are different

3=There is a lot of difference

4=a whole lot different

The panelists may go back and forth between the two samples as much as they need to form an opinion.

3. Arm Wash Method for Measuring Intensity of Perfume

1. The standard arm wash procedure set forth in Analytical Method 1 is followed.

2. Panelists are asked to evaluate odor of a test product and a control product at intervals of 0 minutes, about 30 minutes, about 60 minutes and about 120 minutes according to the following scale:

0=no perfume odor

25=slight perfume odor

50=moderate perfume odor

100=strong perfume odor

The panelists can assign any number between 0 and 100. The numbers 0, 25, 50 and 100 are only intended as guidelines and are not to be viewed as the only numbers that can be assigned.

EXAMPLES

The following non-limiting examples illustrate the composition of the present invention.

Example 1

Liquid shower gel compositions are prepared as follows:
Shower Gel Test Product

About fifteen (15) grams JR-30M polymer is added to about 750 grams distilled water at room temperature. The solution is stirred overnight until JR-30M polymer is fully hydrated and solution becomes clear.

About five (5) grams of volatile perfume A is mixed in about five (5) grams phenyltrimethicone. Then (10) grams perfume-silicone mixture is added in about eighty (80) grams of the hydrated JR-30M solution to form a premix. The composition of the premix is listed in Table 1.

TABLE 1

Composition Premix

| Perfume A | 5.55% |
| Phenytrimethicone | 5.56% |
| Polymer JR-30M | 1.74% |
| Water | 87.15% |
| Total | 100.00% |

The Shower Gel Test Product is made by mixing about 30 grams of the premix from Table 1 into about 70 grams of a shower gel base.
Shower Gel Control Product A Shower Gel Control Product is made by mixing about 28.3 grams distilled water into about 70 grams of the shower gel base and then adding about 1.67 grams of volatile perfume A. The composition of the Shower Gel Control Product and the Shower Gel Test Product are listed in Table 2.

TABLE 2

Compositions of Shower Gels

| Ingredient | Shower Gel Control Product | Shower Gel Test Product |
| --- | --- | --- |
| Na Alkyl Glycerol Ether Sulfonate | 4.28 | 4.28 |
| Coco Betaine | 2.24 | 2.24 |
| Polymer JR-30M (premixed with perfume) | — | 0.60 |
| Phenyltrimethicone | — | 1.67 |
| Perfume A | 1.67 | 1.67 |
| Water and optional ingredients | qs | qs |
| Total | 100.00 | 100.00 |

The total perfume deposition on the skin for the Shower Gel Control Product and for the Shower Gel Test Product is measured according to the GC/MS Method hereinbefore described in the Analytical Methods section. The total perfume deposition on-skin for the Shower Gel Control Product and the Shower Gel Test Product is set forth in Table 3.

TABLE 3

Total Perfume Deposition on-Skin

| Shower Gel Control Product | Shower Gel Test Product |
| --- | --- |
| 15.1 ng | 84.2 ng |

The perfume deposition of the Shower Gel Test Product is five times higher than the deposition of the Shower Gel Control Product.

The perfume intensity of the Shower Gel Test Product and the Shower Gel Control Product is also analyzed according to the Arm Wash Method and the Wash Cloth Method, both hereinbefore described in the Analytical Methods section. The intensity of the perfume for each shower gel according to the Arm Wash Method is set forth in Table 4, and the intensity of the perfume for each shower gel according to the Wash Cloth Method is set forth in Table 5.

TABLE 4

Arm Wash Method Perfume Intensity

| | Shower Gel Control Product | Shower Gel Test Product |
| --- | --- | --- |
| Initial | 49 | 78 |
| 30 mins | 29 | 66 |
| 60 mins | 20 | 60 |
| 120 mins | 13 | 45 |

The intensity of the perfume in the Shower Gel Test Product is about 59% higher than the Shower Gel Control Product initially, about 128% higher than the Shower Gel Control Product after about 30 minutes, about 200% higher than the Shower Gel Control Product after about 60 minutes, and about 246% higher than the Shower Gel Control Product after about 120 minutes according to the Arm Wash Method.

TABLE 5

Wash Cloth Method Perfume Intensity (Initial)

| Shower Gel Control Product | Shower Gel Test Product |
|---|---|
| 26 | 48 |

The intensity of the perfume in the Shower Gel Test Product is about 85% higher than the intensity of the perfume in the Shower Gel Control Product according to the Wash Cloth Method.

Example 2

Liquid shower gel compositions are prepared as follows:

Shower gel Test Product:

About ten (10) grams JR-30M polymer is added to about 490 grams distilled water at room temperature. The solution is stirred overnight until JR-30M polymer is fully hydrated and solution becomes clear.

About 0.20 grams of volatile Perfume B is added to about 15 grams of the hydrated JR-30M polymer solution to form a premix. The composition of the premix is set forth in Table 6.

TABLE 6

Composition of premix

| Ingredient | Premix |
|---|---|
| Perfume B | 1.32% |
| Polymer JR-30M | 1.97% |
| Water | 96.71% |
| Total | 100.00% |

About 15.20 grams of the premix is then mixed with about 34.80 grams of a shower gel base composition to form Shower Gel Test Product A. The composition of Shower Gel Test Product A is set forth in Table 7.

Shower Gel Control Product

Shower Gel Control Product is prepared by mixing about 15 grams distilled water into about 34.80 grams of the same shower gel base composition used for Shower Gel Test Product, and then adding about 0.20 grams of volatile Perfume B. The composition of Shower Gel Control Product is also set forth in Table 7.

TABLE 7

Compositions Shower Gels

| Ingredient | Shower Gel Control | Shower Gel Test Product |
|---|---|---|
| Sodium Laureth Sulfate | 5.80 | 5.80 |
| Cocamidopropyl Betaine | 5.15 | 5.15 |
| Sodium Lauroyl Sarcosinate | 0.50 | 0.50 |
| Perfume B | 0.40 | 0.40 |
| Polymer JR-30M (NOT Premixed with Perfume) | — | — |
| Polyquaterium - 10 (premixed with perfume) | 0.60 | |
| Water and optional ingredients | qs | qs |
| Total | 100.00 | 100.00 |

The intensity of the perfume in Shower Gel Test Product and Shower Gel Control Product, measured according to the Wash Cloth Method, is set forth in Table 8.

TABLE 8

Wash Cloth Method Perfume Intensity

| Shower Gel Control Product | Shower Gel Test Product |
|---|---|
| 5 | 43.5 |

The intensity of the perfume in Shower Gel Test Product is 770% higher than the intensity of the perfume in the Shower Gel Control Product according to the Wash Cloth Method.

Example 3

Liquid Shower Gel Compositions are prepared as follows:

Shower Gel Test Products A and B

To prepare Shower Gel Test Product A, about 2.00 grams of JR-30M polymer is added to about 98.00 grams water at room temperature. The solution is stirred overnight until the JR-30M polymer is fully hydrated and the solution becomes clear. Then about 0.50 grams of Volatile Perfume C is added into about 15 grams of the hydrated JR-30M solution to form a premix. The composition of the premix for Shower Gel Test Product A is set forth in Table 9.

To prepared Shower Gel Test Product B, about 5.00 grams of JR-30M polymer is added to about 95 grams water at room temperature. The solution is stirred overnight until the JR-30M polymer is fully hydrated and the solution becomes clear. Then about 0.50 grams of Volatile Perfume C is added into about 8 grams of the hydrated JR-30M solution to form a premix. The composition of the premix for Shower Gel Test Product B is set forth in Table 9.

TABLE 9

Compositions of premix

| Ingredient | Shower Gel Test Product A Premix | Shower Gel Test Product B Premix |
|---|---|---|
| Perfume C | 3.23% | 5.88 |
| Polymer JR-30M | 1.94% | 4.71 |
| Water | 94.83% | 89.41 |
| Total | 100.00% | 100.00 |

Shower Gel Test Product A is made by mixing about 15.50 grams of the Shower Gel Test Product A Premix into about 34.50 grams of a shower gel base. Shower Gel Test Product B is made by mixing about 8.50 grams of Shower Gel Test Product B Premix into about 44.50 grams of the same shower gel base. The compositions of Shower Gel Test Products A and B are set out in Table 10.

Shower Gel Control Product

The Shower Gel Control Product is prepared by mixing about 15 grams of distilled water into the same shower gel base composition used for Shower Gel Test Products A and B, and then adding about 0.50 grams of volatile Perfume C. The composition of Shower Gel Control Product is set forth in Table 10.

TABLE 10

Compositions of Shower Gels

| Ingredient | Shower Gel Control Product | Shower Gel Test Product A | Shower Gel Test Product B |
|---|---|---|---|
| Sodium Laureth Sulfate | 5.80 | 5.80 | 5.80 |
| Cocamidopropyl Betaine | 5.15 | 5.15 | 5.15 |
| Sodium Lauryl Sarcosinate | 0.50 | 0.50 | 0.50 |
| Perfume C | 1.00 | 1.00 | 1.00 |
| Polymer JR-30M (premixed with perfume) | — | 0.60 | 0.80 |
| Water and optional ingredients | qs | qs | qs |
| Total | 100.00 | 100.00 | 100.00 |

The intensity of the perfume for the Shower Gel Control Product and for Shower Gel Test Products A and B, as measured by the Wash Cloth Method hereinbefore described in the Analytical Methods section, are set forth in Table 11.

TABLE 11

Wash Cloth Method Perfume Intensity (Initial)

| Shower Gel Control Product | Shower Gel Test Product A | Shower Gel Test Product B |
|---|---|---|
| 16 | 37 | 26 |

The intensity of the perfume in Shower Gel Test Product A is about 131% higher than the intensity of the perfume in the Shower Gel Control Product. The intensity of the perfume in Shower Gel Test Product B is about 63% higher than the Shower Gel Control Product.

Example 4

Liquid shower gel compositions are prepared as follows:

Shower Gel Test Product

About 2.00 grams Jaguar C-14-S polymer is added to about 98.00 grams distilled water at room temperature. The solution is stirred overnight until the Jaguar C-14-S polymer is fully hydrated and solution becomes clear.

About 0.20 grams of volatile Perfume D is added in about 15 grams of the hydrated Jaguar C-14-S solution to form a premix. The composition of the premix is listed in Table 12.

TABLE 12

Composition of Premix

| Perfume D | 1.32% |
|---|---|
| Polymer Jaguar C-14-S | 1.97% |
| Water | 96.71% |
| Total | 100.00% |

The Shower Gel Test Product is made by mixing about 15.20 grams of the premix from Table 12 into about 34.80 grams of a shower gel base.

Shower Gel Control Product

A Shower Gel Control Product is made by mixing about 15.00 grams distilled water into about 34.50 grams of the shower gel base and then adding about 0.50 grams of volatile perfume D. The composition of the Shower Gel Control Product and the Shower Gel Test Product are listed in Table 13.

TABLE 13

Compositions of Shower Gels

| Ingredient | Shower Gel Control Product | Shower Gel Test Product |
|---|---|---|
| Sodium Laureth Sulfate | 5.80 | 5.80 |
| Cocamidopropyl Betaine | 5.15 | 5.15 |
| Sodium Lauryl Sarcosinate | 0.50 | 0.50 |
| Perfume D | 0.40 | 0.40 |
| Jaguar C-14-S (premixed with perfume) | — | 0.60 |
| Water and optional ingredients | qs | qs |
| Total | 100.00 | 100.00 |

The intensity of the perfume in the Shower Gel Control Product and in the Shower Gel Test Product, as measured by the Wash Cloth Method hereinbefore described in the Analytical methods section, is set forth in Table 14.

TABLE 14

Wash Cloth Method Perfume Intensity (Initial)

| Shower Gel Control Product | Shower Gel Test Product |
|---|---|
| 16 | 32 |

The intensity of the perfume in the Shower Gel Test Product is about 100% higher than the intensity of the perfume in the Shower Gel Control Product.

What is claimed is:

1. A process for preparing liquid personal cleansing gel compositions which compositions provide enhanced perfume deposition on the skin and which compositions provide increased on-skin fragrance longevity, wherein the compositions comprise:

a) from about 0.01% to about 5% of a cationic cellulose;

b) from about 1% to about 80% of a surfactant selected from the group consisting of anionic surfactants, amphoteric surfactants which have been altered to have a negative charge, and mixtures thereof;

c) from about 0.01% to about 5% of a volatile perfume; and d) water;

wherein the ratio of cationic cellulose: group (b) surfactant ranges from about 1:100 to about 1:2;

wherein the process comprises the steps of:

1) forming a premix comprising the cationic cellulose, the volatile perfume and water; and 2) adding the premix to a base personal cleansing composition comprising the group (b) surfactant and water.

2. A process according to claim 1 wherein the surfactant in (b) is an anionic surfactant.

3. A process according to claim 2 wherein the personal cleansing composition is prepared by mixing from about 1% to about 50% of the premix with from about 50% to about 99% of the personal cleansing base composition.

4. A process according to claim 3 wherein the premix comprises from about 0.1% to about 10% of the cationic cellulose, from about 0.1% to about 10% of the volatile perfume and from about 80% to about 99% water.

5. A process according to claim 4 wherein the personal cleansing composition comprises from about 20% to about 95% water.

6. A process according to claim 4 which contains from about 0.5% to about 2% cationic polymer.

7. A process according to claim 6 which contains from about 0.1% to about 4% of a volatile perfume.

8. A process according to claim 7 which contains from about 2% to about 50% anionic surfactant.

9. A process according to claim 8 which contains from about 40% to about 90% water.

10. A process according to claim 9 which additionally contains from about 1% to about 20% of amphoteric surfactant.

11. A process according to claim 10 wherein the ratio of cationic cellulose to anionic surfactant ranges from about 1:15 to about 1:5.

12. A process according to claim 11 wherein the viscosity of the composition ranges from about 100 to about 100,000 centipoise.

13. A process according to claim 12 which comprises from about 1% to about 20% of optional ingredients.

14. A process according to claim 13 wherein the ratio of the anionic:amphoteric surfactant is less than about 2:1.

* * * * *